US007968753B2

(12) United States Patent
Azzawi et al.

(10) Patent No.: US 7,968,753 B2
(45) Date of Patent: Jun. 28, 2011

(54) METHOD FOR THE PRODUCTION OF ORGANIC PEROXIDES BY MEANS OF A MICROREACTION TECHNIQUE

(75) Inventors: Alexander Azzawi, Solingen (DE); Hans-Ernst Mehesch, Essen (DE); Edgar Von Zadow, Velen (DE); Stefan Kirsch, Quedlingburg (DE); Bernhard Wormland, Bocholt (DE); Martin Sondermann, Rhede (DE)

(73) Assignees: Ehrfeld Mikrotechnik BTS GmbH, Wendelsheim (DE); Pergan Hilfsstoffe fur Industrielle Prozesse GmbH, Bocholt (DE)

( * ) Notice: Subject to any disclaimer, the term of this patent is extended or adjusted under 35 U.S.C. 154(b) by 451 days.

(21) Appl. No.: 12/089,908

(22) PCT Filed: Oct. 13, 2006

(86) PCT No.: PCT/EP2006/009898
§ 371 (c)(1),
(2), (4) Date: Jul. 22, 2008

(87) PCT Pub. No.: WO2007/042313
PCT Pub. Date: Apr. 19, 2007

(65) Prior Publication Data
US 2009/0043122 A1 Feb. 12, 2009

(30) Foreign Application Priority Data

Oct. 14, 2005 (DE) .......................... 10 2005 049 294

(51) Int. Cl.
*C07C 409/00* (2006.01)
*C07C 69/66* (2006.01)
*C07C 69/96* (2006.01)
(52) U.S. Cl. .................. 568/566; 560/179; 558/264
(58) Field of Classification Search .................. 568/566; 560/179; 558/264
See application file for complete search history.

(56) References Cited

U.S. PATENT DOCUMENTS

| 4,075,236 | A | * | 2/1978 | Wagle et al. ............. 560/302 |
| 4,222,671 | A | * | 9/1980 | Gilmore ............. 366/337 |
| 4,798,794 | A | * | 1/1989 | Ogura et al. ............. 438/249 |
| 5,021,516 | A | * | 6/1991 | Wheland ............. 525/403 |
| 5,137,369 | A | * | 8/1992 | Hodan ............. 366/340 |
| 5,803,600 | A | * | 9/1998 | Schubert et al. ............. 366/144 |
| 5,904,424 | A | * | 5/1999 | Schwesinger et al. ......... 366/336 |
| 6,082,891 | A | * | 7/2000 | Schubert et al. ............. 366/338 |
| 6,268,523 | B1 | * | 7/2001 | Kramer et al. ............. 560/302 |
| 2003/0055293 | A1 | * | 3/2003 | Wurziger et al. ............. 568/451 |

FOREIGN PATENT DOCUMENTS

| DE | 19741645 A1 | 3/1999 |
| DE | 10103425 A1 | 8/2001 |
| DE | 69618646 T2 | 8/2002 |
| DE | 20304101 U1 | 5/2003 |
| DE | 10 2005 049 294 B4 | 4/2007 |
| WO | 9708142 A1 | 3/1997 |
| WO | WO 97/08142 * | 3/1997 |
| WO | 2004052518 A2 | 6/2004 |
| WO | 2005064335 A2 | 7/2005 |
| WO | WO 2005/079964 A1 | 9/2005 |

OTHER PUBLICATIONS

Opposition filed in DE 10 2005 049 294 (German), Jun. 25, 2009.
Reply to Opposition filed DE 10 2005 049 294 (German), Oct. 27, 2009.
Chart of Opposition Codes (Nov. 10, 2009).
Opposition Filed in DE 10 2005 49 294 (translation) Jun. 25, 2009.
Reply to opposition filed in DE 10 2005 049 294 (translation) Oct. 27, 2009.
Floyd, T. A., et al, "Novel Liquid Phase Microreactors for Safe Production of Hazardous Specialty Chemicals", Microreaction Technology: Industrial Prospects, IMRET 3, Proceedings of the Third International Conference on Microreaction Technology, W. Ehrfeld, editor; Springer, 2000, pp. 171-180.
Schneider, M. A. and Stoessel, F., "A Microreactor-Based System For The Characterization Of Fast Exothermic Reactions In Liquid Phase", IMRET 7: 7th International Conference On Microreaction Technology, Sep. 7-10, 2003, pp. 7-9.
Inque, T., et al, "Microreactor Direct Synthesis of Hydrogen Peroxide from Hydrogen and Oxygen", IMRET 7: 7th International Conference On Microreaction Technology, Sep. 7-10, 2003, pp. 44-46.
Wada, Y., et al, "Multi-Phase Oxidation Reaction and Ozonolysis In The Limit Of Explosion With Multi-Channel Technology", IMRET 7: 7th International Conference On Microreaction Technology, Sep. 7-10, 2003, pp. 346-348.
Translation of claims, DE 10 2005 049 294 B4, Mar. 26, 2009.
Translation of "Prüfungsbescheid" (Examiners Decision) of the Deutsches Patent—und Markenamt (DPMA), German Application No. 10 2005 049 294.0-44, May 29, 2006.
Translation of "Antwort auf Prüfungsbescheid vom 29.05.2006" (Reply to the Examiner's Decision dated May 29, 2006), German Application No. 10 2005 049 294.0-44, Oct. 12, 2006.
Translation of "Prüfungsbescheid" (Examiner's Decision) of the Deutsches Patent—und Markenamt (DPMA), German Application No. 10 2005 049 294.0-44, Jul. 14, 2008.
Translation of "Erteilungsbeschluss" (Decision to Grant a Patent), German Application No. 10 2005 049 294.0-44, Nov. 10, 2008.
PCT/EP2006/009898, International Search Report, Apr. 26, 2007.
PCT/EP2006/009898, International Preliminary Report on Patentability, Apr. 29, 2007.

* cited by examiner

*Primary Examiner* — Sikarl A Witherspoon
(74) *Attorney, Agent, or Firm* — Baker Donelson Bearman, Caldwell & Berkowitz, PC

(57) ABSTRACT

The invention provides a process for efficient and reliable preparation of organic peroxides, preferably dialkyl peroxides, peroxycarboxylic acids, peroxycarboxylic esters, diacyl peroxides, peroxycarbonate esters, peroxydicarbonates, ketone peroxides and perketals with the aid of at least one static micromixer and an apparatus for performing the process.

19 Claims, 1 Drawing Sheet

METHOD FOR THE PRODUCTION OF ORGANIC PEROXIDES BY MEANS OF A MICROREACTION TECHNIQUE

CROSS REFERENCE TO RELATED APPLICATIONS

This is a §371 National Stage Application of PCT/EP/2006/00989 filed Oct. 13, 2006 which claims priority to DE 102005049294.0 filed Oct. 14, 2005.

BACKGROUND OF THE INVENTION

1. Field of the Invention

The invention provides a process for efficient and reliable preparation of organic peroxides, preferably dialkyl peroxides, peroxycarboxylic acids, peroxycarboxylic esters, diacyl peroxides, peroxycarbonate esters, peroxydicarbonates, ketone peroxides and perketals with the aid of at least one static micromixer and an apparatus for performing the process.

2. Description of Related Art

Organic peroxides are very reactive chemical substances. Since they decompose readily to extremely active free radicals and oxygen, they are used as initiators in the plastics and rubber industry. Fields of use of the organic peroxides are the polymerization of monomers for plastics production, the crosslinking and the modification of polymers, and the curing of polyester resins. In addition, organic peroxides are used as oxidizing agents in medical preparations and for complicated chemical syntheses.

A significant feature of organic peroxides is the SADT (Self-Accelerating Decomposition Temperature). It is the lowest temperature at which self-accelerating decomposition in the transport packaging can occur. A dangerous self-accelerating decomposition reaction, and under unfavorable circumstances explosion or fire, can be caused by thermal decomposition at or above the temperature specified. Contact with incompatible substances and also increased mechanical stress can cause decomposition at or below the SADT.

Organic peroxides are now prepared by continuous or batchwise processes (Chem. Ztg. 98 (tg. 12), 583 (1974), W. Mayr. Ullmann's encyclopedia of industrial chemistry, 6th edition, vol.25, 463 (2002)), DE 698 12 430 T2, DE 699 04 337 T2 or else U.S. Pat. No. 6,268,523. A typical example is the preparation of tert-butyl peroxy-2-ethylhexanoate. This organic peroxide is prepared from tert-butyl hydroperoxide and 2-ethylhexanoyl chloride at a temperature below 35° C. (=SADT) and an average residence time of up to 2 hours in a 500 kg reaction batch in a stirred tank. Specifically, the following illustrative reaction schemes are relevant for the preparation of individual peroxide classes:

Acid chlorides and hydrogen peroxide form diacyl peroxides:

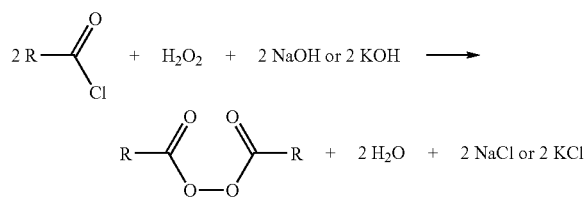

Chloroformates and hydrogen peroxide form peroxydicarbonates:

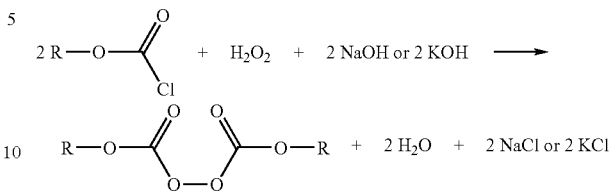

Acid chlorides and organic hydroperoxides form peroxyesters:

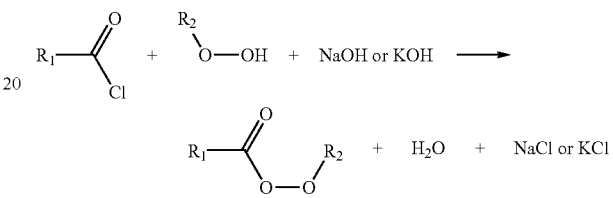

Chloroformates and organic hydroperoxides form percarbonate esters:

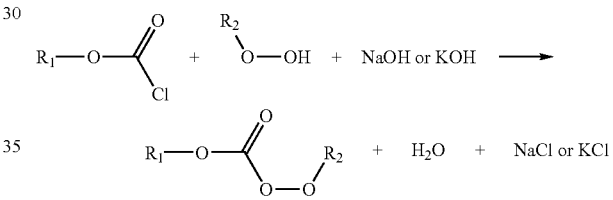

where R is any organic radical.

A significant parameter in the preparation of organic peroxides is optimal temperature control while maintaining the required residence time for the reaction. Experience has shown that the required reaction temperature is in the range of the aforementioned SADT, such that localized exceedance of the reaction temperature in the reactor, which can lead to uncontrollable decomposition of the reaction mixture or of the reaction products, must be prevented. This likewise leads to long reaction times. In the known preparation processes, large amounts of a few hundred liters of the very reactive and explosive reaction mixture accordingly have to be maintained with maximum turbulence in vessels or other reaction systems. This procedure entails a not inconsiderable level of special safety devices, for example in the temperature and turbulence monitoring sector.

Moreover, to increase the reaction safety, the reaction has to be performed at high dilution. This gives rise to a significant additional employment of diluent and a corresponding requirement for downstream removal, purification and workup processes. In addition, this slows the reaction and also the overall preparation process. Furthermore, virtually all preparation methods are biphasic reactions, since the reactants are not entirely miscible with one another. In order to achieve a sufficient reaction rate, intensive finely dispersed mixing of the two phases is necessary. This can be achieved only insufficiently, for example, in a conventional stirred tank reactor. Preparation in other static mixers or tubular reactors is inadvisable, even with incorporation of pressure release devices, for reasons of inhibition of the explosive organic peroxides.

DE 69618646 T2 discloses continuous and batchwise processes for preparing acyl peroxides. In these processes, vigorous stirring of the reactants by means of jet mixers, static mixers or else ultrasound mixers is intended to avoid problems with the stability of the reaction mixtures.

In the continuous processes, yields up to a maximum of 95.5% can be achieved, while the advantage is at shorter reaction times in the batchwise processes, but this is at the expense of the product yield.

Accordingly, no process which enables the preparation of organic peroxides without the above-described disadvantages, i.e. safe and rapid preparation in a high yield, is known in the prior art.

SUMMARY OF THE INVENTION

It was therefore an object of this invention to find a process in which safe process control is possible at low dilution and maximum finely dispersed mixing of the reactants. In addition, an apparatus suitable for this process should also be provided. At the same time, the reactants must be reacted with one another with exact temperature control and monitoring. It should be noted that not all reactants are completely miscible with one another and the two phases therefore have to be constantly mixed intensively with one another for a rapid reaction. In addition, the downstream phase separation, purification and workup processes should be carried out with optimization of the aforementioned parameters in the field of process and safety technology.

It has now been found that, surprisingly, the disadvantages of the prior art processes can be eliminated by performing the preparation of organic peroxides, preferably dialkyl peroxides, peroxycarboxylic acids, peroxycarboxylic esters, diacyl peroxides, peroxycarbonate esters, peroxydicarbonates, ketone peroxides and perketals, in at least one static micromixer.

DETAILED DESCRIPTION OF A PREFERRED EMBODIMENT

Figure 1:
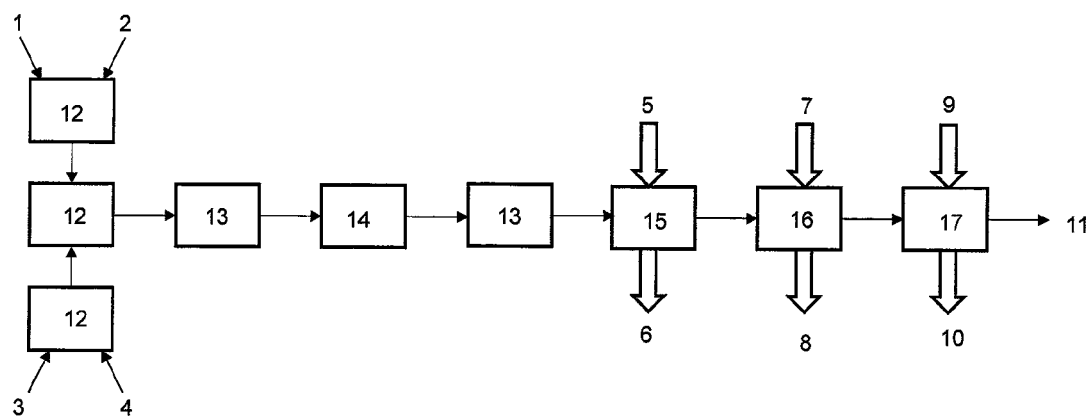
FIG. 1 is a diagram illustrating an embodiment of the present invention.

The use of static micromixers allowed the safety of the preparation process to be increased significantly. In the apparatus used, small amounts per unit volume of the problematic reaction and workup mixture have to be handled, and exact temperature control prevents an undesired rise in the temperature. In addition, the efficiency of the process is enhanced, since, owing to the very high heat exchange area per unit volume, it is possible to work with more highly concentrated reaction and workup mixtures, and the temperature can be increased without the expected relatively high heat of reaction leading to safety problems. Surprisingly, the significantly more concentrated conditions in the microreaction system do not lead to problems as a result of solid intermediates formed from the liquid reactants, as is the case in conventional processes, because these intermediates are converted further very rapidly to the liquid products. When the products formed in the reaction are solids, specific microreactors which are insensitive to blockage should be used. The intensive mixing of the phases additionally leads to an acceleration of the preparation and workup reactions, and to improved reaction conversion and an increase in the yield of the main reaction. The reaction and process control in the microreaction system is far superior to conventional methods for preparing the products in terms of efficiency and safety technology.

The process according to the invention additionally enables, by virtue of the combination of the actual reaction with the workup and the drying of the product which is difficult to handle, a safe and effective reaction in a simple manner.

The present invention therefore provides a process for preparing organic peroxides using hydrogen peroxide or hydroperoxide, at least one base or acid and at least one ketone, alcohol, acid chloride/anhydride and/or chloroformate, which is performed in at least one static micromixer.

The organic peroxides are preferably dialkyl peroxides ($R_1$—O—O—$R_2$), for example di-tert-butyl peroxide, di(2-tert-butylperoxyisopropyl)benzene or dicumyl peroxide, peroxycarboxylic acids ($R_1$—C(O)—O—OH), for example peroxyacetic acid, peroxycarboxylic esters ($R_1$—C(O)—O—O—$R_2$), for example tert-butyl peroxypivalate, tert-butyl peroxy-2-ethylhexanoate, diacyl peroxides ($R_1$—C(O)—O—O—C(O)—$R_2$), for example dibenzoyl peroxide, di(3,5,5-trimethylhexanoyl) peroxide, peroxycarbonate esters ($R_1$O—C(O)—O—O—$R_2$), for example tert-butyl peroxyisopropylcarbonate, tert-butyl peroxy-2-ethylhexylcarbonate, peroxydicarbonates ($R_1$—O—C(O)—O—O—C(O)—$R_2$), for example di(4-tert-butylcyclohexyl) peroxydicarbonate, di(2-ethylhexyl) peroxydicarbonate or dicetyl peroxydicarbonate, ketone peroxides, for example cyclohexanone peroxide, methyl isobutyl ketone peroxide or methyl ethyl ketone peroxide, and/or perketals, for example 2,2-bis(tert-butylperoxy)butane, 1,1-di-tert-butylperoxy-3,3,5-trimethylcyclohexane or 1,1-bis(tert-butylperoxy)cyclohexane, where $R_1$ and $R_2$ in all cases are any organic radicals.

In a preferred embodiment of the invention, two or more reactants are mixed intensively in one or more microstructured static mixers, the temperature of the reaction mixture is optionally controlled at various points in the process in one or more microstructured heat exchangers, then flows through one or more delay volumes for complete performance of the reaction, and the process is preferably combined with the workup of the product and the final drying of the organic peroxide.

Useable hydroperoxides in the context of the invention are all common known compounds, for example alkyl hydroperoxides, such as tert-butyl hydroperoxide or cumene hydroperoxide. These reactants are commercially available or can be prepared by the known oxidation processes, for example the oxidation of cumene with oxygen to prepare cumene hydroperoxide or the acid-catalyzed oxidation of the corresponding alcohol with hydrogen peroxide.

Suitable bases are likewise all bases known in the prior art. Preference is given to NaOH, KOH and/or Ca(OH)$_2$ or imidazoles, for example methylimidazole.

Acids in the context of the invention are all known organic and inorganic acids. Preference is given to sulfuric acid, acetic acid or hydrochloric acid.

The ketones used in the process according to the invention may likewise be all ketones known to those skilled in the art. Preference is given to 3,3,5-trimethylcyclohexanone, methyl ethyl ketone and methyl isobutyl ketone.

The alcohols useable in the context of the invention are also all common compounds. Preference is given to methanol, ethanol, tert-butanol, 2-phenylpropan-2-ol, but also diols, for example bis(α-hydroxyisopropyl)benzene.

The type of acid chlorides used for the process according to the invention is likewise not limited. Preference is given, for example, to 2-ethylhexanoyl chloride, 3,5,5-trimethylhexanoyl chloride or benzoyl chloride.

It is likewise possible to use all known acid anhydrides, for example acetic anhydride or maleic anhydride.

The chloroformates used in the context of the invention may likewise be all compounds known in the prior art. Preference is given, for example, to 2-ethylhexyl chloroformate, isopropyl chloroformate or n-butyl chloroformate.

The concentrations of the agents used may vary greatly.

Preferred concentrations are from 10 to 50% for the bases, from 70 to 100% for the organic peroxide components, and from 30 to 70% for $H_2O_2$.

In a preferred embodiment of the invention, phlegmatizing agents or solvents can be added. Suitable substances for this purpose are particularly isododecane, white oil or phthalates such as diisobutyl phthalate.

Further additives and assistants, for example emulsifiers, may likewise be added to the reactants.

For the process according to the invention, it is possible to use all known static micromixers. In a preferred embodiment of the invention, the static mixers used are multilamination mixers, split and recombine mixers, or else mixers with a cross-sectional constriction. Preference is given here to using static mixers which are flowed through continuously. These include, for example, stack mixers (according to DE 202 06 371 U1) or slotted plate mixers (according to WO 2004 052518 A2), or else comb mixers (according to DE 202 09 009 U1), as supplied, for example, by Ehrfeld Mikrotechnik BTS GmbH. These are multilamination mixers, in which the two fluid streams to be mixed are fanned out into a multitude of thin lamellae or films, and these lamellae are then merged with one another in alternation, such that diffusion and secondary flows result in rapid mixing.

Likewise possible are V-type mixers, as supplied, for example, by Forschungszentrum Karlsruhe, split and recombine mixers, for example cascade mixers or faceted mixers, as supplied by Ehrfeld Mikrotechnik BTS GmbH, or caterpillar mixers, for example obtainable from the Institut für Mikrotechnik Mainz, in which the product streams to be mixed are divided into smaller flows and these small flows are repeatedly combined and divided, or else mixers with a cross-sectional constriction, such as focus mixers or cyclone mixers, or else jet mixers (according to EP 1 165 224 B 1), for example obtainable from Synthesechemie, and impingement jet mixers or valve mixers (as described in WO 2005/079964 A1), obtainable from Ehrfeld Mikrotechnik BTS GmbH.

In a preferred embodiment of the invention, micromixers with channel widths of less than 500 µm, preferably less than 200 µm, more preferably less than 100 µm, are used.

In such micromixers, the reactant mixtures are preferably metered in by means of precise and low-pulsation pumps, for example HPLC pumps or syringe pumps. The reaction mixture thus mixed is more preferably subsequently passed through an arrangement of microstructured heat exchangers and delay volumes with a given residence time. The arrangement is preferably configured such that the temperature profile in the flowing reaction mixture along the flow direction is adjustable by virtue of the sequence of heat exchangers and delay zones.

For the process according to the invention, preference is given to using all known microstructured heat exchangers. Known heat exchangers include micro-heat exchangers which consist of stacked thin plates provided with many microchannels and welded to one another. The base geometry of such heat exchangers is preferably approximately cubic, heat transfer performances in the range of 100 kW being achievable in the case of an edge length of, for example, 3 cm, as described, by way of example, in $2^{nd}$ International Conference on Microreaction Technology, Tropical Conference Preprints, (ISBN 0-8169-9945-7, p. 88-95).

Such microstructured heat exchangers are, for example, crosscurrent or countercurrent plate heat exchangers, as described in DE 37 09 278 A1, and as obtainable, for example, from Ehrfeld Mikrotechnik BTS GmbH. Owing to their long and very narrow channels, however, these heat exchangers are highly sensitive to solid particles, since even small particles in the reaction medium can block these channels. These heat exchangers are thus preferably used when the occurrence of particles can be ruled out at the intended point in the process.

When the occurrence of particles has to be expected, preference is given to using microstructured heat exchangers whose narrowest passage is sufficiently wide that the particles can pass unhindered. Such a heat exchanger is, for example, the tubular temperature control module from Ehrfeld Mikrotechnik BTS GmbH. The tubular heating control module consists of concentric tubes which are flowed through by the fluid in a countercurrent configuration. This arrangement is flowed through by the heating medium both in the core and in the outer region. This design corresponds in principle to the way in which an intensive cooler functions.

In a preferred embodiment of the process according to the invention, the static micromixer is flowed through continuously, the reaction mixture is brought to the suitable temperature by means of heat exchangers and then the reaction mixture is optionally fed into a heatable delay volume, remains there for a time determined by the delay volume and the flow rate of the reaction mixture, and the starting materials which may be present as immiscible phases are constantly mixed intensively with one another within this delay volume.

Useful heat exchangers for the process according to the invention include apparatus in which tubes aligned at right angles to the flow are incorporated into the casing flowed through by the reaction mixture, and are flowed through by a heat carrier medium or heated electrically. To increase the heat transfer, such tubes are appropriately arranged offset from one another in several planes in the direction of the main flow. In the case of heat exchanger modules which are designed for aqueous reaction media and volume flows in the region of 1000 l/h and have a casing cross-sectional area of about 100 $cm^2$, tubes having an external diameter in the range of a few millimeters, which are arranged at a distance of less than one millimeter, are advantageously used. Such high-performance micro-heat exchangers reach transfer performances of a few 10 s of kW, have low pressure drops and are moreover easy to clean.

In another type of high-performance micro-heat exchanger, plate-shaped bodies which are electrically heated or, as hollow bodies, flowed through by a heat carrier medium are installed into the casing flowed through by the reaction mixture. Such micro-plate heat exchangers typically have plate separations in the sub-millimeter range, and the plates can be deinstalled and cleaned in a simple manner. As in the case of the above-described micro-tube bundle heat exchanger, heat transfer performances of a few 10 s of kW are also achieved here in the case of appropriate boundary conditions.

The delay volume or else the delay structure in the context of the invention comprises delimited volumes which, owing to their internal volume, can be flowed through within a given time, for example capillaries or else microstructured static mixers. It is possible to use different delay volumes which each feature a very narrow delay time distribution and have low dead volumes. The temperature of these delay volumes can preferably be controlled by installing electrical heaters or cooling devices or by virtue of a temperature control fluid circulating around the delay volume.

In the simplest case, the delay volume consists of a capillary of a given length, but it is also possible to use other volumes or arrangements which are flowed through uniformly.

A particularly suitable arrangement is one composed of delay volumes in which a static mixer, preferably a microstructured static mixer, for mixing multiphase mixtures is in each case installed between volumes flowed through in one direction.

In a further preferred embodiment of the invention, in this delay structure, there is constant finely dispersed mixing of the immiscible reactants by means of one or more static mixers or by virtue of high-frequency mechanical action, for example that of ultrasound, on a defined delay structure, or by virtue of a combination of one or more static mixers and high-frequency mechanical action. The term "high-frequency" encompasses frequencies in the range from 10 kHz to 20 MHz.

At suitable points in the reaction region, preference is given to using temperature sensors and microstructured heat exchangers for the exact control and maintenance of the reaction and processing temperature. Only by using microstructured heat exchangers can it be ensured that the reaction mixture does not exceed the critical decomposition temperature, even when the reaction temperature is close to this decomposition temperature.

Likewise particularly suitable is an arrangement in which the delay volumes can be subjected to high-frequency vibrations by virtue of directly mounted ultrasound oscillators or by virtue of immersion of the delay volumes into a bath, or by attaching piezo modules.

It is likewise possible to use delay structures in which the mixture is pumped in circulation analogously to a loop reactor, in which case one or more microstructured static micromixers are optionally inserted into the circuit.

The temperature profile in the flowing reaction mixture along the flow direction is preferably established by a sequence of heat exchangers and delay volumes.

The reaction temperature depends on the reactants used and is preferably in the range of 10-70° C.

After passing through the delay volumes, it is advantageous when the peroxide is sent to a workup. This is preferably designed analogously to the reaction apparatus technology.

The workup of the organic peroxide to be prepared is subdivided preferably into the region for removal of the organic peroxide from the aqueous mother liquor and that for purification of the organic peroxide and the subsequent phase separation. In the purification, the crude product and the wash solutions are fed in defined flow rates to a micromixer, preferably a static micromixer, and mixed intensively there. Subsequently, this mixture is preferably fed into a delay volume, the temperature of which is preferably controllable, where it remains for a time determined by the volume of the delay structure and the flow rate of the reaction mixture. In addition, in this delay structure, a constant finely dispersed mixing of the immiscible reactants is ensured by means of one or more static mixers or by virtue of high-frequency action, for example that of ultrasound, on a defined delay structure, or by virtue of a combination of one or more static mixers and high-frequency action.

After the wash has been performed, the forced emulsion formed is preferably separated in a separator, principally a micro-separation module, into the particular phases for further workup.

After the aforementioned workup, the water is preferably removed from the liquid organic peroxide in a drying process. According to the prior art, this drying can be undertaken by means of desiccants, for example zeolites, magnesium sulfate, magnesium chloride, etc., or by means of dried air or another dry gas, in a countercurrent or crosscurrent. In the drying to be undertaken here, the organic peroxide is fed at defined flow rates to a micro-extraction mixer, preferably a static micro-extraction mixer, in countercurrent to dried air and mixed intensively there. Subsequently, the water-containing air or the water-containing gas is sent to further workup steps, and the organic peroxides thus prepared are sent to transfer and finishing steps.

The invention also provides an apparatus for performing the process according to the invention, comprising at least one micromixer (12), at least one heat exchanger (13) and optionally a delay volume (14).

The invention will be illustrated in detail by the diagrams below and the examples which follow, without being restricted thereto.

WORKING EXAMPLES

The working examples which follow were performed in an apparatus according to FIG. 1. For this purpose, the reactants (1) and (2) are first mixed by means of a cascade mixer from Ehrfeld Mikrotechnik BTS GmbH (EMB), a split and recombine mixer having 5 cascades and a maximum channel width of 500 μm as the static micromixer (12). Reactant (3) is added to this mixture in a cascade mixer as a further micromixer (12). Optionally, a phlegmatizing agent (4) is added to (3) before it is mixed in an EMB LH 25 slotted plate mixer with channels arranged in lamellar form with a channel width of from 25 to 50 μm as a static micromixer (12). The reactants (1), (2), (3) and optionally (4) thus premixed then pass through a tubular temperature control module from Ehrfeld Mikrotechnik BTS GmbH as a heat exchanger (13), then remain in a capillary as a delay volume (14) and optionally pass through a further tubular temperature control module (13). From there, they pass through extraction stages (15), (16) and (17), where (15) and (16) consist of a cascade mixer from Ehrfeld Mikrotechnik BTS GmbH, a settler as a separator and optionally a tubular temperature control module from Ehrfeld Mikrotechnik BTS GmbH in a different number of stages, and the drying stage (17) consists of a cascade mixer from EMB and a settler as a separator. The following compounds/temperatures were used:

| No. | Stream | Temperature |
|-----|--------|-------------|
| 1 | Base or acid | 0-25° C. |
| 2 | Hydroperoxide or hydrogen peroxide | 10-25° C. |
| 3 | Ketone, acid chloride or chloroformate | 10-25° C. |
| 4 | Phlegmatizing agent | 10-25° C. |
| 5 | Water | 5-25° C. |
| 6 | Mother liquor of the reaction | 0-25° C. |
| 7 | Wash solutions (up to 4 different) | 0-25° C. |
| 8 | Wastewater from wash steps (up to 4 steps) | 0-25° C. |
| 9 | Dried air | −15-0° C. |
| 10 | Laden waste air | −10-25° C. |
| 11 | Product | −10-25° C. |
| 12 | Static micromixer | |
| 13 | Heat exchanger | |

| No. | Stream |
|---|---|
| 14 | Delay volume |
| 15 | Extraction stage composed of mixer, separator and optionally heat exchanger |
| 16 | Extraction stage composed of mixer, separator and optionally heat exchanger (up to 4 stages) |
| 17 | Drying stage composed of mixer and separator |

Example 1

Preparation of tert-butyl peroxy-2-ethylhexanoate

The tert-butyl peroxy-2-ethylhexanoate was prepared in a system as shown in FIG. 1 with a total reaction volume of 75 ml. At temperatures in the reaction zone of 40-55° C., the following test parameters were established:

| No. | Stream | Temperature | Mass flow rate |
|---|---|---|---|
| 1 | Potassium or sodium hydroxide solution (10-50%) | 0-25° C. | 4.2-21.1 g/min |
| 2 | tert-butyl hydroperoxide (70-100%) | 10-25° C. | 3.0-4.5 g/min |
| 3 | 2-ethylhexanoyl chloride | 10-25° C. | 4.6 g/min |
| 7 | Sodium hydroxide solution (10%), bisulfite solution (10%), bicarbonate solution (5%) and sodium acetate solution (5%) | 0-25° C. | In each case 8.0 g/min |
| 8 | Wastewater from wash steps | 0-25° C. | In each case 8.0 g/min |
| 9 | Dried air | −15-0° C. | 6.0-8.0 g/min |
| 10 | Laden waste air | −10-25° C. | 6.2-8.3 g/min |
| 11 | tert-butyl peroxy-2-ethylhexanoate | −10-25° C. | 6.1 g/min |

The tert-butyl peroxy-2-ethylhexanoate was in this case prepared at a mass yield greater than 90% with a product quality of more than 99% of peroxide content.

Example 2

Preparation of tert-butyl peroxy-2-ethylhexanoate by Means of Use of methylimidazole Using 1-methylimidazole, tert-butyl peroxy-2-ethylhexanoate was prepared in a system as shown in FIG. 1 with a total reaction volume of 25 ml. At temperatures in the reaction zone of 25-35° C. without addition of water upstream of the reaction zone, the following test parameters were established:

| No. | Stream | Temperature | Mass flow rate |
|---|---|---|---|
| 1 | 1-methylimidazole | 0-25° C. | 1.2-4.0 g/min |
| 2 | tert-butyl hydroperoxide (70-100%) | 10-25° C. | 0.76-1.1 g/min |
| 3 | 2-ethylhexanoyl chloride | 10-25° C. | 1.54 g/min |
| 5 | Water | 5-25° C. | 7.0-28.0 g/min |
| 6 | Mother liquor of the reaction | 0-25° C. | 8.2-33.0 g/min |
| 7 | Sodium hydroxide solution (10%), bisulfite solution (10%), bicarbonate solution (5%) and sodium acetate solution (5%) | 0-25° C. | In each case 2.9 g/min |
| 8 | Wastewater from wash steps | 0-25° C. | In each case 3.0 g/min |
| 9 | Dried air | −15-0° C. | 6.0-8.0 g/min |
| 10 | Laden waste air | −10-25° C. | 6.2-8.3 g/min |
| 11 | tert-butyl peroxy-2-ethylhexanoate | −10-25° C. | 2.03 g/min |

The tert-butyl peroxy-2-ethylhexanoate was prepared here in a mass yield of greater than 88% with a product quality of more than 95% of peroxide content.

Example 3

Preparation of di(2-ethylhexyl) peroxydicarbonate

The di(2-ethylhexyl) peroxydicarbonate was prepared in a system as shown in FIG. 1 with a total reaction volume of 20 ml. At temperatures in the reaction zone of 30-35° C., the following test parameters were established:

| No. | Stream | Temperature | Mass flow rate |
|---|---|---|---|
| 1 | Potassium or sodium hydroxide solution (10-50%) | 0-25° C. | 0.84-2.1 g/min |
| 2 | Hydrogen peroxide (30-70%) | 10-25° C. | 0.2-0.6 g/min |
| 3 | 2-ethylhexyl chloroformate | 10-25° C. | 1.6 g/min |
| 4 | Isododecane | 10-25° C. | 0.4-0.6 g/min |
| 5 | Water | | |
| 6 | Mother liquor of the reaction | 0-25° C. | 1.26-2.9 g/min |
| 7 | Bicarbonate solution (5%) | 0-25° C. | 1.2 g/min |
| 8 | Wastewater from the wash | 0-25° C. | 1.3 g/min |
| 9 | Dried air | −15-0° C. | 4.1-5.5 g/min |
| 10 | Laden waste air | −10-25° C. | 4.2-5.7 g/min |
| 11 | Di(2-ethylhexyl) peroxydicarbonate | −10-25° C. | 1.38 g/min |

The di(2-ethylhexyl) peroxydicarbonate was prepared here in a mass yield of greater than 92%. The product is present as a blend in isododecane with a peroxide content of 70-85%.

Example 4

Preparation of tert-butyl peroxy-2-ethylhexylcarbonate

The tert-butyl peroxy-2-ethylhexylcarbonate was prepared in a system as shown in FIG. 1 with a total reaction volume of 25 ml. At temperatures in the reaction zone of 55° C., the following test parameters were established:

| No. | Stream | Temperature | Mass flow rate |
|---|---|---|---|
| 1 | Potassium or sodium hydroxide solution (10-50%) | 0-25° C. | 1.4-6.8 g/min |
| 2 | tert-butyl hydroperoxide (70-100%) | 10-25° C. | 1.0-1.5 g/min |
| 3 | 2-ethylhexyl chloroformate | 10-25° C. | 1.7 g/min |
| 5 | Water | | |
| 6 | Mother liquor of the reaction | 0-25° C. | 1.9-7.8 g/min |
| 7 | Sodium hydroxide solution (10%), bisulfite solution (10%), bicarbonate solution (5%) and sodium acetate solution (5%) | 0-25° C. | In each case 3.2 g/min |
| 8 | Wastewater from 1st wash | 0-25° C. | In each case 3.3 g/min |
| 9 | Dried air | −15-0° C. | 6.5-8.7 g/min |
| 10 | Laden waste air | −10-25° C. | 6.6-8.8 g/min |

-continued

| No. | Stream | Temperature | Mass flow rate |
|---|---|---|---|
| 11 | tert-butyl peroxy-2-ethylhexylcarbonate | −10-25° C. | 2.17 g/min |

The tert-butyl peroxy-2-ethylhexylcarbonate was prepared here at a mass yield of greater than 95% with a product quality of more than 93% of peroxide content.

Example 5

Preparation of 1,1-di(tert-butylperoxy)-3,3,5-trimethylcyclohexane

The 1,1-di(tert-butylperoxy)-3,3,5-trimethylcyclohexane was prepared in a system as shown in FIG. 1 with a total reaction volume of 45 ml. At temperatures in the reaction zone of 12-18° C., the following test parameters were established:

| No. | Stream | Temperature | Mass flow rate |
|---|---|---|---|
| 1 | Sulfuric acid (50-98%) | 0-20° C. | 1.4-2.7 g/min |
| 2 | tert-butyl hydroperoxide (70-100%) | 10-20° C. | 2.7-4.0 g/min |
| 3 | 3,3,5-trimethylcyclohexanone | 10-20° C. | 1.89 g/min |
| 5 | Mother liquor of the reaction | 0-25° C. | 2.1-4.71 g/min |
| 6 | Soft water, sodium hydroxide solution (10%) | 0-20° C. | 4.1 g/min and 3.9 g/min |
| 7 | Waste water from wash steps | 0-20° C. | 4.2 g/min and 4.0 g/min |
| 8 | Dried air | | 4.3 g/min and 4.1 g/min |
| 9 | Laden waste air | −15-0° C. | 11.6-15.5 g/min |
| 10 | 1,1-di(tert-butylperoxy)-3,3,5-trimethylcyclohexane | −10-25° C. | 11.9-16.0 g/min |

The 1,1-di(tert-butylperoxy)-3,3,5-trimethylcyclohexane was prepared here in a mass yield of greater than 63% with a product quality of more than 72% of peroxide content.

Example 6

Preparation of di(3,5,5-trimethylhexanoyl) peroxide

The di(3,5,5-trimethylhexanoyl) peroxide was prepared in a system as shown in FIG. 1 with a total reaction volume of 60 ml. At temperatures in the reaction zone of 26-32° C., the following test parameters were established:

| No. | Stream | Temperature | Mass flow rate |
|---|---|---|---|
| 1 | Potassium or sodium hydroxide solution (10-50%) | 0-25° C. | 2.5-12.6 g/min |
| 2 | Hydrogen peroxide (30-70%) | 10-25° C. | 0.6-1.6 g/min |
| 3 | 3,5,5-trimethylhexanoyl chloride | 10-25° C. | 2.7 g/min |
| 5 | Water | | |
| 6 | Mother liquor of the reaction | 0-25° C. | 1.5-14.6 g/min |
| 7 | Sodium hydroxide solution (10%), soft water | 0-25° C. | 2.1 g/min and 1.5 g/min |
| 8 | Wastewater from wash steps | 0-25° C. | 2.3 g/min and 1.6 g/min |
| 9 | Dried air | −15-0° C. | 6.9-9.2 g/min |
| 10 | Laden waste air | −10-25° C. | 7.0-9.4 g/min |
| 11 | Di(3,5,5-trimethylhexanoyl) peroxide | −10-25° C. | <2.3 g/min |

The di(3,5,5-trimethylhexanoyl) peroxide was prepared here at a mass yield greater than 92% with a product quality of more than 91% of peroxide content.

Comparison of the Preparation of Peresters in Conventional Processes and with the Aid of Microreaction Technology

Example 7

Preparation of tert-butyl perpivalate tert-Butyl perpivalate is prepared in the continuous industrial preparation process typically in a 3-stage stirred tank battery with a tank volume of in each case 350 liters with the following parameters:

| No. | Stream | Temperature | Mass flow rate |
|---|---|---|---|
| 1 | Potassium or sodium hydroxide solution (45%) | 20° C. | 3.9 kg/min |
| 2 | tert-butyl hydroperoxide (70%) | 20° C. | 3.5 kg/min |
| 3 | Pivaloyl chloride | 15° C. | 2.7 kg/min |
| 4 | Isododecane | 20° C. | 1.1 kg/min |
| 5 | Sodium hydroxide solution (10%), bisulfite solution (10%), bicarbonate solution (5%) and sodium acetate solution (5%) | 10° C. | In each case 5.8 kg/min |
| 6 | tert-butyl-peroxypivalate (75% in isododecane) | 8° C. | 4.37 kg/min |

The yield in the conventional process is 84.0% of theory.

The tert-Butyl perpivalate was prepared in a microreaction system as shown in FIG. 1 with a total reaction volume of 60 ml. At temperatures in the reaction zone of 14-21° C., the following test parameters were established:

| No. | Stream | Temperature | Mass flow rate |
|---|---|---|---|
| 1 | Potassium or sodium hydroxide solution (10-50%) | 0-20° C. | 1.5-11.0 g/min |
| 2 | tert-butyl hydroperoxide (70-100%) | 10-20° C. | 0.7-3.6 g/min |
| 3 | Pivaloyl chloride | 0-15° C. | 2.7 g/min |
| 4 | Isododecane | 0-25° C. | 0.6-1.1 g/min |
| 5 | Sodium hydroxide solution (10%), bisulfite solution (10%), bicarbonate solution (5%) and sodium acetate solution (5%) | 10° C. | In each case 5.8 g/min |
| 6 | tert-butyl peroxypivalate (75% in isododecane) | −10-20° C. | 4.8 g/min |

The performance of the synthesis in microreaction systems allowed the conversion in the reaction to be improved significantly. The tert-butyl perpivalate thus prepared as a 75% solution in isododecane was typically obtained with a yield of 92.9% based on the acid chloride used.

Comparison of the Preparation of Peroxydicarbonates in Conventional Processes and with the Aid of Microreaction Technology

Example 8

Preparation of Isopropyl peroxydicarbonate

Isopropyl peroxydicarbonate is prepared in a continuous industrial preparation process typically in a 2-stage stirred tank battery with a tank volume of in each case 80 liters with the following parameters:

| No. | Stream | Temperature | Mass flow rate |
|---|---|---|---|
| 1 | Sodium hydroxide solution (32.3%) | 10° C. | 1.08 kg/min |
| 2 | Hydrogen peroxide (20.5%) | 10° C. | 0.76 kg/min |
| 3 | Isopropyl chloroformate | 10° C. | 1.02 kg/min |
| 4 | Diethylene glycol bis(allylcarbonate) | 5° C. | 2.48 kg/min |
| 5 | Wash with water | 5° C. | 1.36 kg/min |
| 6 | Isopropylperoxydicarbonate (20% in isododecane) | 5° C. | 3.72 kg/min |

The yield in the conventional process is 94.0% of theory. The high hydrolysis of the isopropyl chloroformate used demands that the water content in the reaction mixture be kept as low as possible. In the conventional reaction process, this is not achievable for safety reasons. In addition, the mixture of isopropyl peroxydicarbonate with curable optical monomers, as demanded by the manufacturers of optical synthetic glasses, contains an intolerable content of chloride of typically 130-230 ppm.

In the preparation of isopropyl peroxydicarbonate in microreaction systems as shown in FIG. 1 with a total reaction volume of 95 ml, the very rapid mixing of the reactants and the effective removal of the heat of reaction allows performance of the synthesis at 15° C. with considerably less water in the reaction mixture. The following test parameters were established:

| No. | Stream | Temperature | Mass flow rate |
|---|---|---|---|
| 1 | Sodium hydroxide solution (45%) | 10-25° C. | 2.17 g/min |
| 2 | Hydrogen peroxide (50%) | 10-20° C. | 0.85 g/min |
| 3 | Isopropyl chloroformate | 10-20° C. | 2.90 g/min |
| 4 | Diethylene glycol bis(allylcarbonate) | 5-15° C. | 9.66 g/min |
| 5 | Wash with water | 5° C. | 5.05 g/min |
| 6 | Isopropyl peroxydicarbonate (20% in isododecane) | 5° C. | 12.08 g/min |

Surprisingly, in the case of synthesis in microreaction systems, an IPP-diethylene glycol bis(allyl carbonate) mixture was obtained with a peroxide yield of more than 99% and a chloride content of less than 10 ppm in a 12% blend. It has thus been possible to develop a simple and safe process for preparing isopropyl peroxydicarbonate in diethylene glycol bis(allylcarbonate), which additionally satisfies the high quality demands of the manufacturers of optical plastic lenses.

Comparison of the Preparation of Ketone Peroxides in Conventional Processes and with the Aid of Microreaction Technology

Example 9

Preparation of Methyl Isobutyl Ketone Peroxide

In the industrial preparation process, methyl isobutyl ketone peroxide is prepared typically in batches of size 600-900 kg at 20-25° C. and reaction time from 2 to 3 hours with the following parameters:

| No. | Stream | Temperature | Mass |
|---|---|---|---|
| 1 | Methyl isobutyl ketone | 20° C. | 160-290 kg |
| 2 | Hydrogen peroxide (70%) | 20° C. | 270-490 kg |
| 3 | Sulfuric acid (78%) | 20° C. | 14-25 kg |
| 4 | Isododecane | 20° C. | 80-120 kg |
| 5 | Methyl isobutyl ketone peroxide (isomer mixture) | 20° C. | 220-400 kg |

In the conventional process, the resulting product has an active oxygen of approx. 11.0%.

The methyl isobutyl ketone peroxide was prepared in a microreaction system as shown in FIG. 1 with a total reaction volume of 170 ml. At temperatures in the reaction zone of 22-30° C., the following test parameters were established:

| No. | Stream | Temperature | Mass flow rate |
|---|---|---|---|
| 1 | Methyl isobutyl ketone | 15-30° C. | 4.8 g/min |
| 2 | Hydrogen peroxide (70%) | 20-25° C. | 2.36 g/min |
| 3 | Sulfuric acid (96%) | 10-25° C. | 0.11 g/min |
| 4 | Isododecane | 5-30° C. | 2.2 g/min |
| 5 | Methyl isobutyl ketone peroxide (isomer mixture) | 20-25° C. | 11.22 g/min |

A product with approx. 11.6% active oxygen is obtained. The performance of the synthesis in microreaction systems allowed the conversion of the reactants to the ketone peroxide to be enhanced by 47% at 25° C. and residence time 5.8 minutes, even though the amount of hydrogen peroxide used, in relation to the ketone, had been reduced by 50% compared to the conventional process.

Comparison of the Preparation of tert-butyl Peroxycarbonates in Conventional Processes and with the Aid of Microreaction Technology

Example 10 tert-Butyl Peroxyisopropylcarbonate tert-Butyl peroxyisopropylcarbonate is prepared in a continuous industrial preparation process typically in a 3-stage stirred tank battery with a volume of in each case 350 liters with the following parameters:

| No. | Stream | Temperature | Mass flow rate |
|---|---|---|---|
| 1 | Potassium hydroxide solution (45%) | 15° C. | 3.3 kg/min |
| 2 | tert-butyl hydroperoxide (70%) | 15° C. | 3.3 kg/min |
| 3 | Isopropyl chloroformate | 10° C. | 2.3 kg/min |

-continued

| No. | Stream | Temperature | Mass flow rate |
|---|---|---|---|
| 4 | Isododecane | 15° C. | 0.7 kg/min |
| 5 | Soft water | 15° C. | 4.0 kg/min |
| 6 | Sodium hydroxide solution (10%), bisulfite solution (10%), bicarbonate solution (5%) and sodium acetate solution (5%) | 10° C. | In each case 6.1 kg/min |
| 7 | tert-butyl peroxyisopropylcarbonate (75% in isododecane) | 10° C. | 3.71 kg/min |

The yield in the conventional process is 84.0% of theory.

The tert-butyl peroxyisopropylcarbonate was prepared in a microreaction system as shown in FIG. 1 with a total reaction volume of 175 ml. At temperatures in the reaction zone of 19-31° C., the following test parameters were established:

| No. | Stream | Temperature | Mass flow rate |
|---|---|---|---|
| 1 | Potassium hydroxide solution (45%) | 15-25° C. | 4.11 g/min |
| 2 | tert-butyl hydroperoxide (70%) | 15-25° C. | 4.12 g/min |
| 3 | Isopropyl chloroformate | 10-25° C. | 3.68 g/min |
| 4 | Isododecane | 15-25° C. | 0.7 g/min |
| 5 | Soft water | 15-25° C. | 2.00 g/min |
| 6 | Sodium hydroxide solution (10%), bisulfite solution (10%), bicarbonate solution (5%) and sodium acetate solution (5%) | 10-20° C. | In each case 7.3 g/min |
| 7 | tert-butyl peroxyisopropylcarbonate (86%) in isododecane) | 10-20° C. | 6.09 g/min |

The excess of hydroperoxide used has been reduced by 28% in this process compared to the conventional method. The reduction in the water content in the reaction mixture and the associated lower hydrolysis of the isopropyl chloroformate used allowed tert-butyl peroxyisopropylcarbonate to be obtained with 99% peroxide yield in the preparation in microreaction systems.

What is claimed is:

1. A process for preparing an organic peroxide comprising mixing hydrogen peroxide or hydroperoxide, at least one base or acid and at least one ketone, alcohol, acid chloride/acid anhydride and/or chloroformate, in at least one static micromixer.

2. The process as claimed in claim 1, wherein the static micromixer comprises a multilamination mixer, a split and/or recombine mixer, a caterpillar mixer or a mixer with a cross-sectional constriction.

3. The process as claimed in claim 1, wherein the static micromixer has capability of continuous flow through and a mixture therein is brought to a suitable temperature by means of at least one heat exchanger, and then the mixture is optionally fed into a heatable delay structure, and said mixture remains in said delay structure for a time determined by the volume of the delay structure and a flow rate of the mixture, and starting materials for said mixture are optionally present as at least one immiscible phase and said starting materials are constantly mixed intensively with one another within said delay structure.

4. The process as claimed in claim 3, wherein the delay structure is in the form of a static mixer.

5. The process as claimed in claim 3, wherein mixing of the starting materials in the delay structure comprises direct and/or indirect action of high-frequency vibrations.

6. The process as claimed in claim 1, comprising utilizing a micromixer with a channel width of less than 200 μm.

7. The process as claimed in claim 3, wherein the heat exchanger used is a microstructured heat exchanger.

8. The process as claimed in claim 3, wherein the delay structure used is a capillary.

9. The process as claimed in claim 3, wherein the mixture is pumped in circulation in the delay structure, and a static micromixer is optionally included in a circuit therewith.

10. The process as claimed in claim 1, wherein said process has a temperature profile that is adjustable by virtue of a sequence of at least one heat exchanger and/or at least one delay zone.

11. The process of claim 2 wherein the static micromixer has a capability of continuous flow through, and wherein a reaction mixture therein is brought to a temperature by at least one heat exchanger, and the reaction mixture is fed into a heatable delay structure and said reaction mixture remains therein for a time period, and wherein at least one starting material for said mixture is optionally present as at least one immiscible phase, and said starting materials are mixed in said delay structure.

12. The process of claim 11 wherein said delay structure is a static mixer.

13. The process of claim 11 comprising utilizing a micromixer with a channel width of less than 200 μm.

14. The process of claim 3 comprising utilizing a micromixer with a channel width of less than 200 μm.

15. The process of claim 4 comprising utilizing a micromixture with a channel width of less than 200 μm.

16. The process as claimed in claim 1 comprising heating the mixture flowing through at least one plate-shaped body installed into a casing through which a mixture flows, the plate-shaped body
   (i) is electrically heated or,
   (ii) is at least one hollow body through which a heat carrier medium is capable of flowing.

17. The process as claimed in claim 1, wherein the organic peroxide comprises di-tert-butyl peroxide, di(2-tert-butylperoxyisopropyl)benzene, dicumyl peroxide, peroxyacetic acid, tert-butyl peroxypivalate, tert-butyl peroxy-2-ethylhexanoate, dibenzoyl peroxide, di(3,5,5-trimethylhexanoyl) peroxide, tert-butyl peroxyisopropylcarbonate, tert-butyl peroxy-2-ethylhexylcarbonate, di(4-tert-butylcyclohexyl) peroxydicarbonate, di(2-ethylhexyl) peroxydicarbonate, dicetyl peroxydicarbonate, cyclohexanone peroxide, methyl isobutyl ketone peroxide, or methyl ethyl ketone peroxide, 2,2-bis(tert-butylperoxy)butane, 1,1-di-tert-butylperoxy-3,3,5-trimethylcyclohexane, or 1,1-bis(tert-butylperoxy)cyclohexane.

18. The process as claimed in claim 1, wherein the organic peroxide comprises tert-butyl peroxy-2-ethylhexanoate, di(2-ethylhexyl) peroxydicarbonate, tert-butyl peroxy-2-ethylhexylcarbonate, 1,1-di(tert-butylperoxy)-3,3,5-trimethylcyclohexane, di(3,5,5,-trimethylhexanoyl) peroxide, tert-butyl perpivalate, isopropyl peroxydicarbonate, methyl isobutyl ketone peroxide, or tert-Butyl peroxyisopropylcarbonate.

19. The process as claimed in claim 3, wherein the suitable temperature comprises a range of 10-70° C.

* * * * *